United States Patent
Ritchart et al.

[19]

[11] Patent Number: 6,017,316
[45] Date of Patent: Jan. 25, 2000

[54] VACUUM CONTROL SYSTEM AND METHOD FOR AUTOMATED BIOPSY DEVICE

[75] Inventors: Mark A. Ritchart, Murrieta; Fred H. Burbank, San Juan Capistrano; Seth A. Foerster; John L. Wardle, both of San Clemente, all of Calif.

[73] Assignee: Biopsys Medical, Irvine, Calif.

[21] Appl. No.: 08/878,468

[22] Filed: Jun. 18, 1997

[51] Int. Cl.⁷ .................................................. A61B 10/00
[52] U.S. Cl. ........................... 600/567; 600/562; 600/565
[58] Field of Search ..................................... 600/566, 562, 600/564, 565, 567; 604/22, 27

[56] References Cited

U.S. PATENT DOCUMENTS

| | | |
|---|---|---|
| Re. 33,258 | 7/1990 | Onik et al. . |
| Re. 34,056 | 9/1992 | Lindgren et al. . |
| 2,705,949 | 4/1955 | Silverman . |
| 2,919,692 | 1/1960 | Ackermann . |
| 3,001,522 | 9/1961 | Bucalo . |
| 3,590,808 | 7/1971 | Muller . |
| 3,606,878 | 9/1971 | Kellogg, Jr. . |
| 3,732,858 | 5/1973 | Banko . |
| 3,734,099 | 5/1973 | Bender et al. . |
| 3,844,272 | 10/1974 | Banko . |
| 4,099,518 | 7/1978 | Baylis et al. . |
| 4,200,106 | 4/1980 | Douvas et al. . |
| 4,203,444 | 5/1980 | Bonnell et al. . |
| 4,210,146 | 7/1980 | Banko . |
| 4,243,048 | 1/1981 | Griffin . |
| 4,306,570 | 12/1981 | Matthews . |
| 4,461,305 | 7/1984 | Cibley . |
| 4,517,977 | 5/1985 | Frost . |
| 4,600,014 | 7/1986 | Beraha . |
| 4,644,951 | 2/1987 | Bays . |
| 4,651,753 | 3/1987 | Lifton . |
| 4,681,123 | 7/1987 | Valtchev . |
| 4,699,154 | 10/1987 | Lindgren . |
| 4,702,260 | 10/1987 | Wang . |
| 4,702,261 | 10/1987 | Cornell et al. . |
| 4,708,147 | 11/1987 | Haaga . |
| 4,729,764 | 3/1988 | Gualtier . |
| 4,733,671 | 3/1988 | Mehl . |
| 4,735,215 | 4/1988 | Goto et al. . |
| 4,781,202 | 11/1988 | Janese . |
| 4,844,088 | 7/1989 | Kambin . |
| 4,850,373 | 7/1989 | Zatloukal et al. . |
| 4,893,635 | 1/1990 | de Groot et al. . |
| 4,919,146 | 4/1990 | Rhinehart et al. . |

(List continued on next page.)

FOREIGN PATENT DOCUMENTS

| | | |
|---|---|---|
| 0378692 | 7/1990 | European Pat. Off. . |
| 0442851 | 8/1991 | European Pat. Off. . |
| C935625 | 5/1955 | Germany . |

(List continued on next page.)

OTHER PUBLICATIONS

"When it Comes to Core Samples, I Demand Accuracy and Consisancy for All My Patients" Bard Radiology.
"Nucleotome System" Surgical Dynamics.
"ASAP Automatic Soft Tissue Biopsy System" Microvasive Boston Scientific Corporation.

*Primary Examiner*—Richard J. Apley
*Assistant Examiner*—Justine R. Yu

[57] ABSTRACT

An automatic control system for a vacuum-assisted automatic core biopsy device (10) is provided, wherein the automatic core biopsy device (10) comprises a housing (12), out of which extends a needle assembly (14) including a hollow outer piercing needle (16), an inner cutter (18) having a lumen (20), a probe housing (22), and a tissue receiving notch (24). The automatic control system (92) is computerized to move the hollow outer piercing needle (16) automatically to the target tissue lesion, as was true in the prior art, but also is programmed to automatically control the rotational orientation of the piercing needle (16), and its associated tissue receiving notch (24), as well as the axial positioning and rotation of the cutting cannula (18). Consequently, a clinician user need only mark the desired locations within the target location from which tissue samples are desired and the automatic control system will operate the device to retrieve samples from the marked locations.

23 Claims, 17 Drawing Sheets

U.S. PATENT DOCUMENTS

| | | |
|---|---|---|
| 4,924,878 | 5/1990 | Nottke . |
| 4,940,061 | 7/1990 | Terwilliger et al. . |
| 4,944,308 | 7/1990 | Akerfeldt . |
| 4,958,625 | 9/1990 | Bates et al. . |
| 4,966,583 | 10/1990 | Debbas . |
| 4,971,067 | 11/1990 | Bolduc et al. . |
| 4,976,269 | 12/1990 | Mehl . |
| 4,991,592 | 2/1991 | Christ . |
| 5,005,585 | 4/1991 | Mazza . |
| 5,031,634 | 7/1991 | Simon . |
| 5,048,538 | 9/1991 | Terwilliger et al. . |
| 5,108,381 | 4/1992 | Kolozsi . |
| 5,111,828 | 5/1992 | Kornberg et al. . |
| 5,125,413 | 6/1992 | Baran . |
| 5,133,359 | 7/1992 | Kedem . |
| 5,133,360 | 7/1992 | Spears . |
| 5,148,813 | 9/1992 | Bucalo . |
| 5,172,700 | 12/1992 | Bencini et al. . |
| 5,174,300 | 12/1992 | Bales et al. . |
| 5,183,052 | 2/1993 | Terwilliger . |
| 5,183,054 | 2/1993 | Burkholder et al. . |
| 5,188,118 | 2/1993 | Terwilliger . |
| 5,195,533 | 3/1993 | Chin et al. . |
| 5,197,484 | 3/1993 | Kornberg et al. . |
| 5,217,458 | 6/1993 | Parins . |
| 5,217,479 | 6/1993 | Shuler . |
| 5,224,470 | 7/1993 | Schnepp-Pesch et al. . |
| 5,224,488 | 7/1993 | Neuffer . |
| 5,234,000 | 8/1993 | Hakky et al. . |
| 5,243,994 | 9/1993 | Ranalletta . |
| 5,249,583 | 10/1995 | Mallaby . |
| 5,255,688 | 10/1993 | Gilliard . |
| 5,282,476 | 2/1994 | Terwilliger . |
| 5,284,156 | 2/1994 | Schramm et al. . |
| 5,301,684 | 4/1994 | Ogirala . |
| 5,313,958 | 5/1994 | Bauer . |
| 5,316,013 | 5/1994 | Striebel, II et al. . |
| 5,320,110 | 6/1994 | Wang . |
| 5,324,300 | 6/1994 | Elias et al. . |
| 5,333,619 | 8/1994 | Burgio . |
| 5,335,672 | 8/1994 | Bennett . |
| 5,336,176 | 8/1994 | Yoon . |
| 5,341,816 | 8/1994 | Allen . |
| 5,348,022 | 9/1994 | Leigh et al. . |
| 5,353,804 | 10/1994 | Kornberg et al. . |
| 5,368,045 | 11/1994 | Clement et al. . |
| 5,415,169 | 5/1995 | Siczek . |
| 5,526,822 | 6/1996 | Burbank et al. . |
| 5,584,292 | 12/1996 | Cheung . |
| 5,602,449 | 2/1997 | Krause et al. . |
| 5,775,333 | 7/1998 | Burbank et al. ........................ 600/567 |

FOREIGN PATENT DOCUMENTS

| | | |
|---|---|---|
| 2018601 | 10/1979 | United Kingdom . |
| WO90/08508 | 8/1990 | WIPO . |
| 9314707 | 8/1993 | WIPO . |
| WO93/14700 | 8/1993 | WIPO . |
| 9322972 | 11/1993 | WIPO . |
| WO96/24289 | 8/1996 | WIPO . |

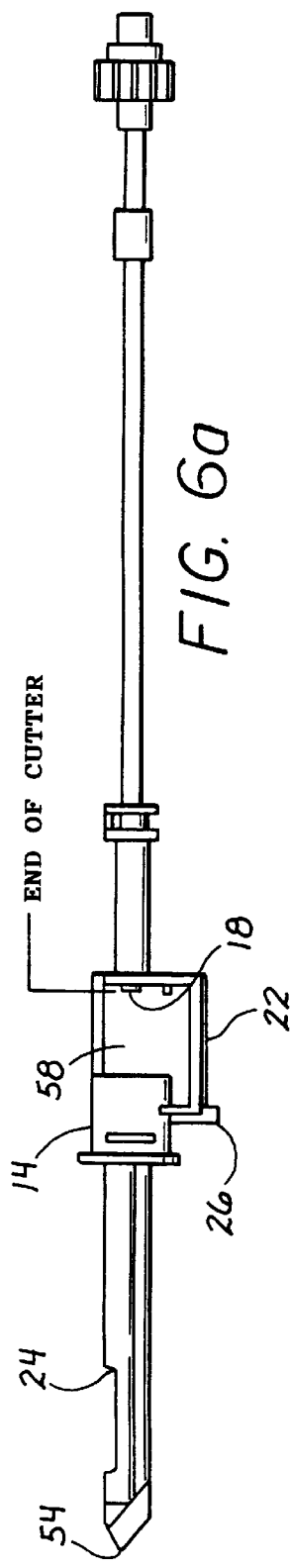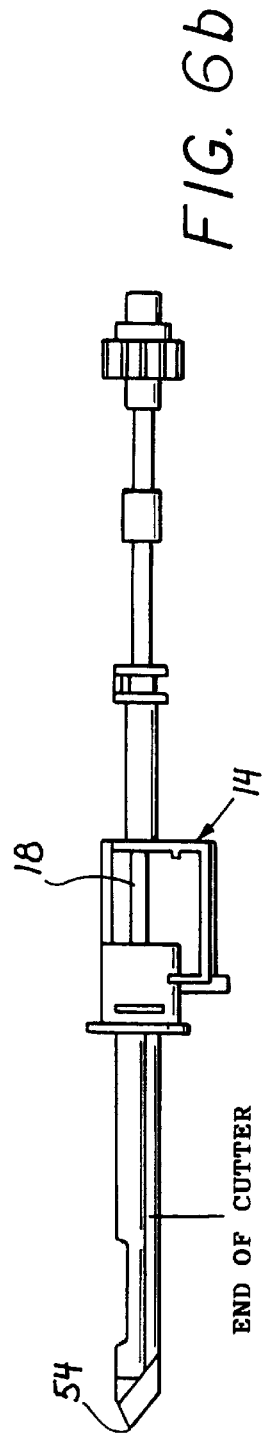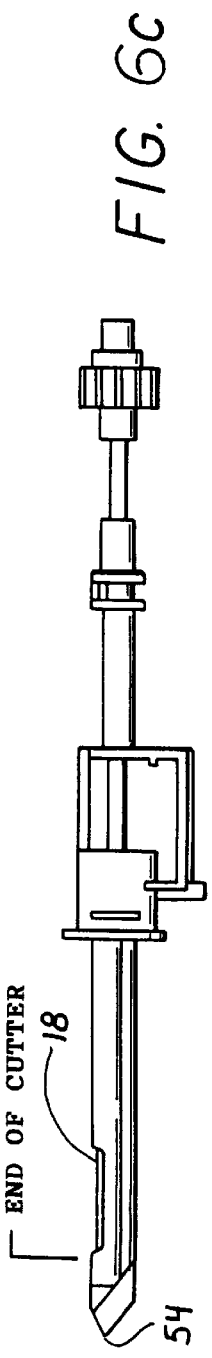

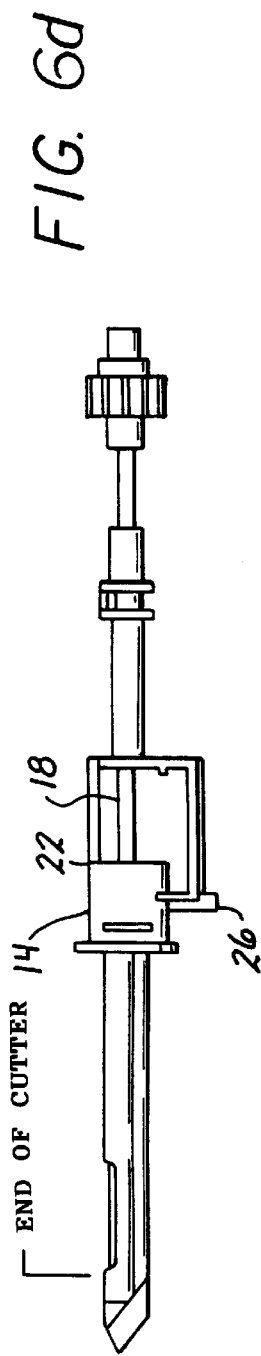
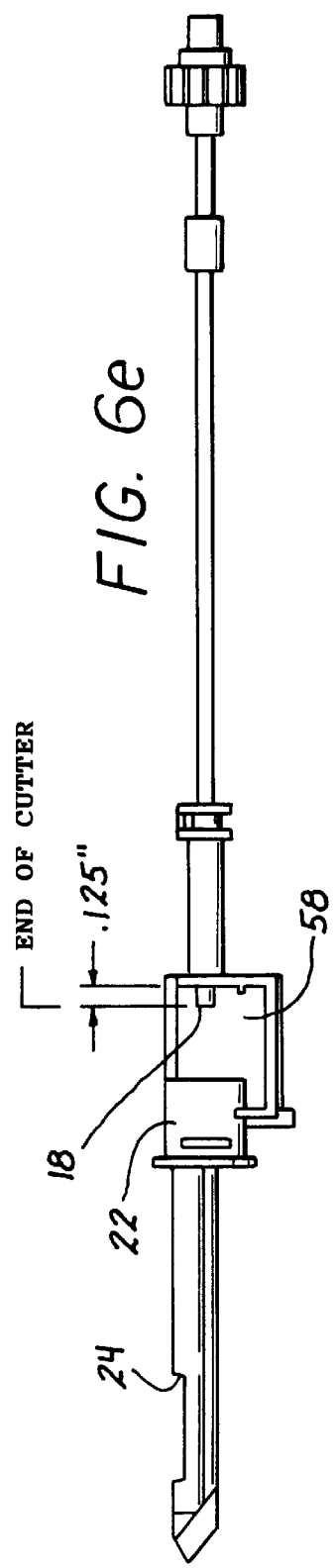
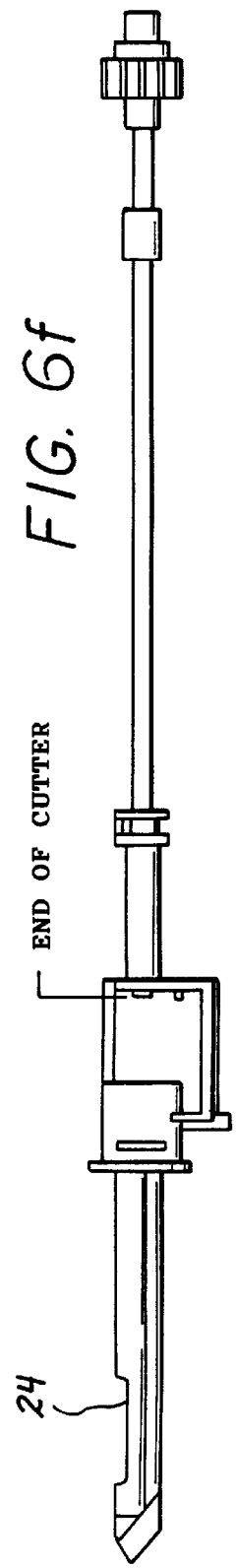

| VALVE DESIG-NATION | VALVE STATE (REF. FIG. 5) | | | | | |
|---|---|---|---|---|---|---|
| | CUTTER FULLY RETRACTED TO START POSITION FIG. 6a CUTTER POSITION ① | CUTTER NEAR PROX. EDGE OF TISSUE NOTCH W/CUTTER MOTOR ACTIVATED FIG. 6b CUTTER POSITION ② | CUTTER @ DISTAL MOST POSITION IMMEDIATELY AFTER CUTTER MOTOR STOPS FIG. 6c CUTTER POSITION ③ | BEGIN REWARD RETRACTION OF CUTTER FROM DISTAL POSITION FIG. 6d CUTTER POSITION ④ | SHORT DISTANCE FROM PROX. WALL OF CASSETTE HOUSING FIG. 6e CUTTER POSITION ⑤ | CUTTER IN FULLY RETRACTED START POSITION FIG. 6f CUTTER POSITION ⑥ |
| A | CLOSED | OPEN | CLOSED | CLOSED | CLOSED | CLOSED |
| B | CLOSED | CLOSED | CLOSED | CLOSED | OPEN | OPEN |
| C | OPEN | CLOSED | OPEN | OPEN | CLOSED | CLOSED |
| D | OPEN | CLOSED | CLOSED | OPEN | OPEN | OPEN |
| E | CLOSED | OPEN | OPEN | OPEN | CLOSED | CLOSED |

FIG. 7

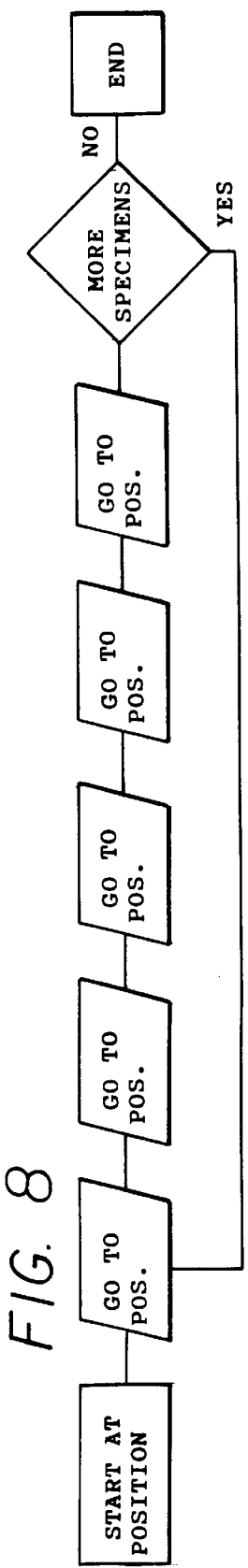

FIG. 8

|  |  | VALVE STATE (REF. FIG. 14) | | | | | |
|---|---|---|---|---|---|---|---|
| | | FIG. 6a CUTTER POSITION ① | FIG. 6b CUTTER POSITION ② | FIG. 6c CUTTER POSITION ③ | FIG. 6d CUTTER POSITION ④ | FIG. 6e CUTTER POSITION ⑤ | FIG. 6f CUTTER POSITION ⑥ |
| VALVE DESIG-NATION | A | CLOSED | OPEN | CLOSED | CLOSED | CYCLING ON AND OFF | CYCLING ON AND OFF |
| TO DISTAL PORT | C | OPEN | CLOSED | OPEN | OPEN | CLOSED | CLOSED |
| TO PROXIMAL PORT | B | OPEN | CLOSED | CLOSED | CLOSED | OPEN | OPEN |
| | D | CLOSED | OPEN | OPEN | OPEN | CLOSED | CLOSED |

FIG. 15

VACUUM CONTROL SYSTEM AND METHOD FOR AUTOMATED BIOPSY DEVICE

CROSS-REFERENCE TO RELATED APPLICATIONS

This application is related to co-pending applications Ser. No. 08/386,941, entitled Methods and Devices for Automated Biopsy and Collection of Soft Tissue, filed Feb. 10, 1995 and Ser. No. 08/568,143, entitled Control System and Method for Automated Biopsy Device, filed Dec. 6, 1995. These applications are herein expressly incorporated by reference.

FIELD OF THE INVENTION

The present invention relates to methods and devices for tissue sampling, and more specifically to improved vacuum control systems and methods for biopsy instruments.

BACKGROUND OF THE INVENTION

It is often desirable and frequently necessary to sample or test a portion of tissue from humans and other animals, particularly in the diagnosis and treatment of patients with cancerous tumors, pre-malignant conditions, and other diseases and disorders. Typically, in the case of cancer, when the physician establishes by means of procedures such as palpation, x-ray, or ultrasound imaging that suspicious circumstances exist, a biopsy is performed to determine whether the cells are cancerous. Biopsy may be done by an open or percutaneous technique. Open biopsy, which is an invasive surgical procedure using a scalpel and involving direct vision of the target area, removes the entire mass (excisional biopsy) or a part of the mass (incisional biopsy). Percutaneous biopsy, on the other hand is usually done with a needle-like instrument through a relatively small incision, blindly or with the aid of an artificial imaging device, and may be either a fine needle aspiration (FNA) or a core biopsy. In FNA biopsy, individual cells or clusters of cells are obtained for cytologic examination and may be prepared such as in a Papanicolaou smear. In core biopsy, as the term suggests, a core or fragment of tissue is obtained for histologic examination which may be done via a frozen section or paraffin section.

The type of biopsy utilized depends in large part on circumstances present with respect to the patient, and no single procedure is ideal for all cases. However, core biopsy is extremely useful in a number of conditions and is being used more frequently by the medical profession.

One particular type of image guided percutaneous core breast biopsy instrument currently available is a vacuum-assisted automatic core biopsy device. One such successful biopsy device is shown and disclosed in U.S. Pat. No. 5,526,822, to Burbank et al., which is expressly incorporated by reference herein, and in the previously referenced related patent application Ser. No. 08/386,941, both of which are commonly owned by the assignee of the present application, and is presently commercially available under the trademark MAMMOTOME. This device includes a piercing cannula and a cutting cannula and has the capability to actively capture tissue prior to cutting the tissue, meaning that vacuum pressure is used to "draw" the tissue into a capture notch. Mechanisms are included for rotationally orienting the piercing cannula, which has a tissue capture notch near the distal end thereof, so that the notch is in a desired angular orientation for receiving a tissue sample. Additional mechanisms permit the cutting cannula to travel axially, so that it may be retracted and advanced as desired and rotationally, in order to assist the cutting process. Active capture allows for sampling through non-homogeneous tissues, meaning that the device is equally capable of cutting through hard and soft tissue. The device also includes means to direct and position the cutting chamber in arbitrary positions about and along its longitudinal axis, means for rapid and atraumatic removal of an arbitrary number of core samples with only a single insertion into the body and organ, and means for coding and decoding the location from which the samples were obtained. Together, these capabilities allow for more complete sampling of large lesions and for the complete removal of small lesions. This type of instrument is advantageous in that it permits the obtainment of a plurality of tissue samples from different locations with only a single instrument insertion. Consequently, a wide area of tissue within the body may be excised through a single small opening, so as to greatly reduce resultant trauma to the patient. Use of this kind of instrument also produces high quality samples in a manner which does not require direct handling of the samples by the operator.

Presently, vacuum-assist automatic core biopsy devices of the type disclosed in the aforementioned '822 patent have been manually operated once the piercing cannula of the device is located as desired adjacent to a target lesion. In particular, vacuum pressure has typically been applied simultaneously to both the vacuum and cutter lumens during a procedure by manually operating a source of vacuum pressure when a region of vacuum adjacent to the tissue receiving notch is desired It would thus be a significant advantage to be able to automatically control the application of vacuum pressure during the procedure, so that the user is free to entirely concentrate on the medical procedure itself and in order to enhance the accuracy and efficiency of the procedure.

It has been found through usage of vacuum-assist automatic core biopsy devices of this type that vacuum management techniques are valuable not only for drawing tissue into the capture notch, but also to assist in transport of the tissue specimen proximally through the instrument and out of the patient's body. To elaborate, because of differential pressures developed within the biopsy probe during the course of the procedure, efficient transport of the tissue specimen outside of the body does not always occur. For example, sometimes as the cutter is retracted, the specimen remains at the distal section of the probe and thus inside the body. If pressure at the proximal end of the specimen can be established that is lower than the pressure at the distal end of the specimen, a favorable pressure differential will exist which will improve the likelihood that the tissue specimen will travel proximally with the cutter to the designated tissue receptacle.

During a tissue specimen removal procedure, a significant quantity of blood and small excess tissue pieces are generated by the cutting process. Presently, this blood and tissue is drawn back through the cutter lumen when vacuum is applied thereto to assist in retrieving the tissue specimen, and exits from the proximal end of the device in the vicinity of the tissue specimen receptacle. This is a problem in that it obscures the practitioner's view of the specimen as it is being retrieved, and additionally complicates the objective of obtaining an intact specimen. It would therefore be a further advantage to be able to operate the vacuum system so that such blood and tissue is effectively removed to a site remote from that of the tissue specimen receptacle, and in such a manner that it does not interfere with the effective obtainment of intact specimens. Furthermore, it would be yet another advantage to be able to selectively apply differential vacuum pressure throughout the probe, automatically, in order to in order to assist in the removal of clogging debris from the various lumens and ports.

SUMMARY OF THE INVENTION

This invention accomplishes the aforementioned objective by providing a biopsy device having an automatic control system for selectively delivering vacuum pressure to the region of the tissue receiving notch during the course of the biopsy procedure. Using the inventive system, vacuum pressure is delivered selectively responsive to the position of the cutter, thereby maximizing operational efficiency and ensuring the acquisition of an optimized tissue specimen and minimizing system clogging.

More particularly, in one aspect of the invention an automatic biopsy device is provided which comprises a first elongate cannula having a distal end for entering tissue and a notch disposed proximally of the distal end for receiving a portion of the tissue which is positioned adjacent to the notch. A second elongate cannula is disposed coaxially with the first cannula, and is slidable along the first cannula for cutting the portion of tissue protruding into the notch when the second cannula slides past the notch, thereby depositing the portion of cut tissue within the first elongate cannula proximal to the first cannula distal end. A source of vacuum pressure is provided for selectively delivering vacuum pressure to the region within the first elongate cannula adjacent to the notch. At least one passage, and preferably two, including both a vacuum lumen and a lumen extending through the second elongate cannula, fluidly connects the source of vacuum pressure to the region adjacent to the notch. Advantageously, a controller is provided which is programmed to automatically control the flow of vacuum pressure to the region during a biopsy procedure, such that the ability to successfully obtain and transport a tissue sample proximally from the notch to a tissue sample receptacle is enhanced.

In another aspect of the invention, an automatic biopsy device is provided which includes a cannula having a distal end for entering tissue and a notch disposed in the distal end for receiving a portion of the tissue which is positioned adjacent to the notch. A cutter operable for cutting the portion of tissue protruding into the notch is provided, so that the portion of cut tissue is deposited into the distal end of the first cannula. Also included are a proximally disposed tissue receiving chamber, a source of vacuum pressure for selectively delivering vacuum pressure to the region within the first elongate cannula adjacent to the notch, and a passage for fluidly connecting the source of vacuum pressure to the region adjacent to the notch. A valve controls the flow of vacuum pressure through the passage, the valve being controlled automatically by a controller between an open state and a closed state to thereby selectively control the flow of vacuum pressure to the region during a biopsy procedure.

In yet another aspect of the invention, a method of controlling vacuum pressure to an automatic biopsy device is disclosed, wherein the device comprises a first cannula having a distal end for entering tissue and a tissue-receiving notch, a second cutting cannula having a distal end and being disposed coaxially with the first cannula, the second cannula having a lumen, a source of vacuum pressure, a vacuum lumen communicating with a region in the first cannula adjacent to the notch, a distal aspiration port communicating with the vacuum lumen, and a proximal aspiration port communicating with the second cannula lumen. The inventive method includes the step of opening both the vacuum lumen and the cutting cannula lumen to the flow of vacuum pressure when the distal end of the cutting cannula is disposed proximal to the notch, before severing of a tissue sample has commenced. Once the distal end of the cutting cannula has traversed distally of the notch and the tissue sample has been severed, the vacuum lumen is closed to the flow of vacuum pressure. Finally, the cutting cannula lumen is closed to the flow of vacuum pressure once the distal end of the cutting cannula, carrying the tissue specimen, has been withdrawn proximally to a location to which the tissue specimen is to be delivered.

The invention, together with additional features and advantages thereof, may best be understood by reference to the following description taken in conjunction with the accompanying illustrative drawing.

BRIEF DESCRIPTION OF THE DRAWING

FIGS. 6a, 6b, 6c, 6d, 6e, and 6f are elevational schematic views illustrating a typical operational sequence for an automated biopsy probe performing a biopsy procedure;

FIG. 7 is a table indicating the valve state in each vacuum supply line during each sequential position of the biopsy probe illustrated in FIGS. 6a through 6f, according to the embodiment illustrated in FIG. 5;

FIG. 8 is a logic diagram illustrating the preferred control scheme for the operational sequence shown in FIGS. 6a through 6f, including the option to repeat the sequence without removing the biopsy probe from a patients body;

FIG. 15 is a table similar to that of FIG. 7, indicating the condition of each vacuum supply line during each sequential position of the biopsy probe illustrated in FIGS. 6a through 6f, according to the embodiment shown in FIG. 14.

DESCRIPTION OF THE INVENTION

Figure 1:
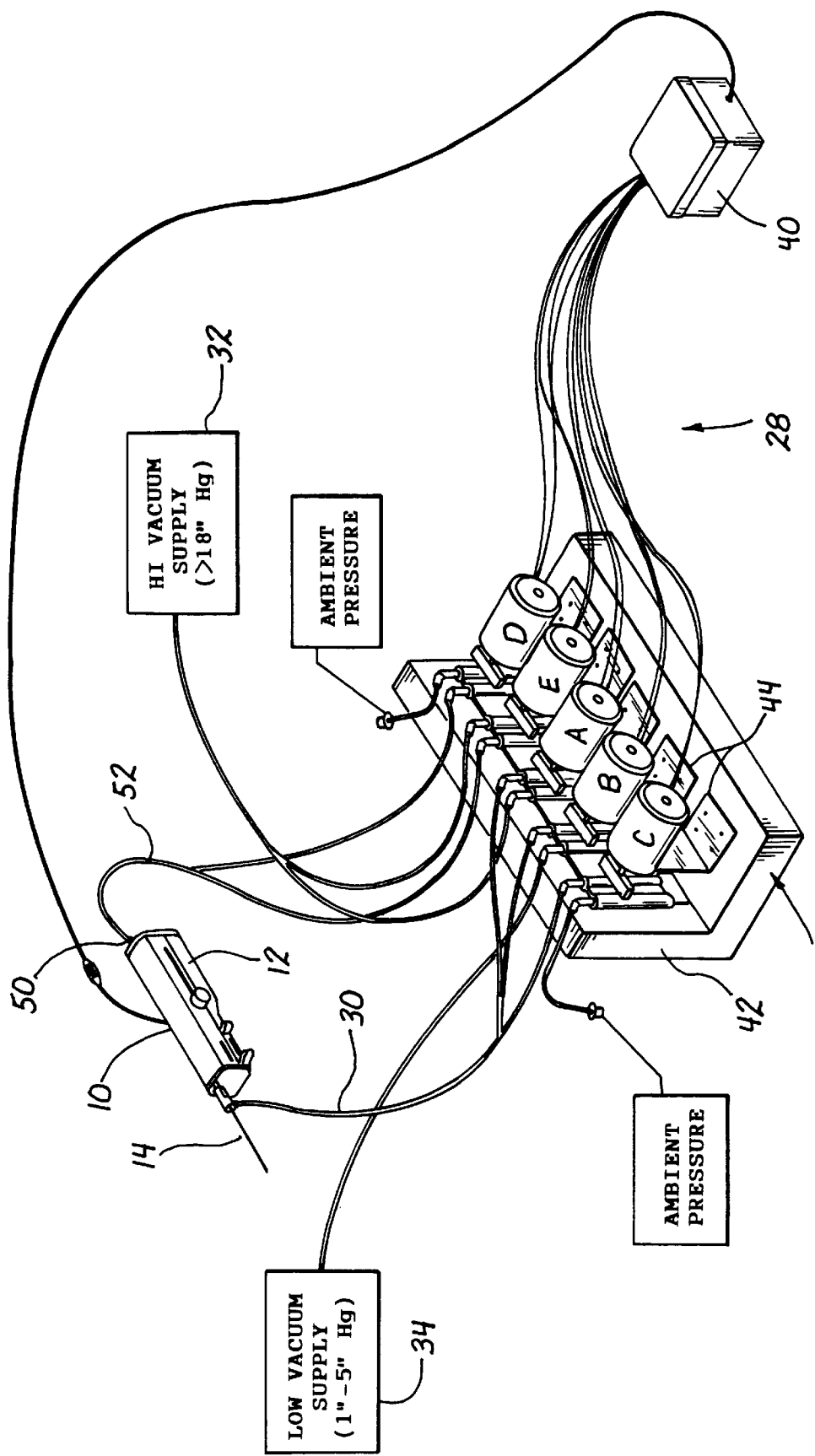
FIG. 1 is a perspective view schematically illustrating a vacuum control system for an automatic core biopsy device constructed in accordance with the principles of the present invention.
Figure 16:
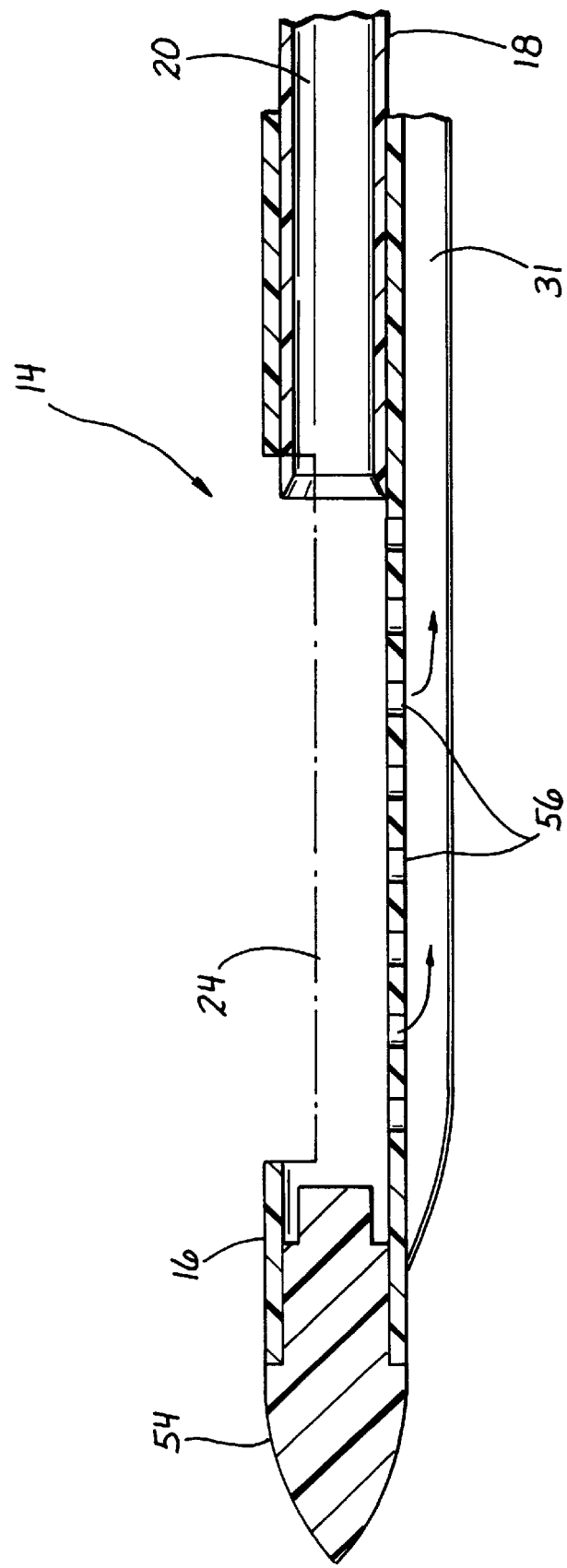
FIG. 16 is a cross-sectional view of the hollow outer piercing needle and cutter assembly for the automatic core biopsy device illustrated in FIG. 1.

Referring now more particularly to FIGS. 1 and 16, an automatic core biopsy device 10, preferably of the type disclosed in U.S. Pat. No. 5,526,822 and related patent application Ser. No. 08/386,941, both of which are herein expressly incorporated by reference, is illustrated. The biopsy instrument 10 comprises a housing 12, from which extends a needle assembly or probe body 14. The biopsy instrument is illustrated in more detail, schematically and with the housing 12 removed, in FIGS. 5 and 6a through 6f. Viewing these figures, the probe body 14 includes an outer cannula 16, which may comprise a hollow outer piercing needle, or may alternatively have a blunt distal end, if desired, an inner cutter 18 having a lumen 20 (FIG. 16), a tissue cassette housing 22 and a tissue receiving notch 24. A distal aspiration fitting or port 26 is adapted for attachment to a vacuum pressure control system 28 (FIG. 1) through a tube or tubing 30 (FIG. 5). in order to aspirate or apply vacuum to the notch 24. The vacuum is supplied through a separate vacuum lumen 31 (FIG. 16) extending along the length of the outer cannula 16, and through the lumens of the outer cannula 16 or the inner cutter 18.

Figure 3:
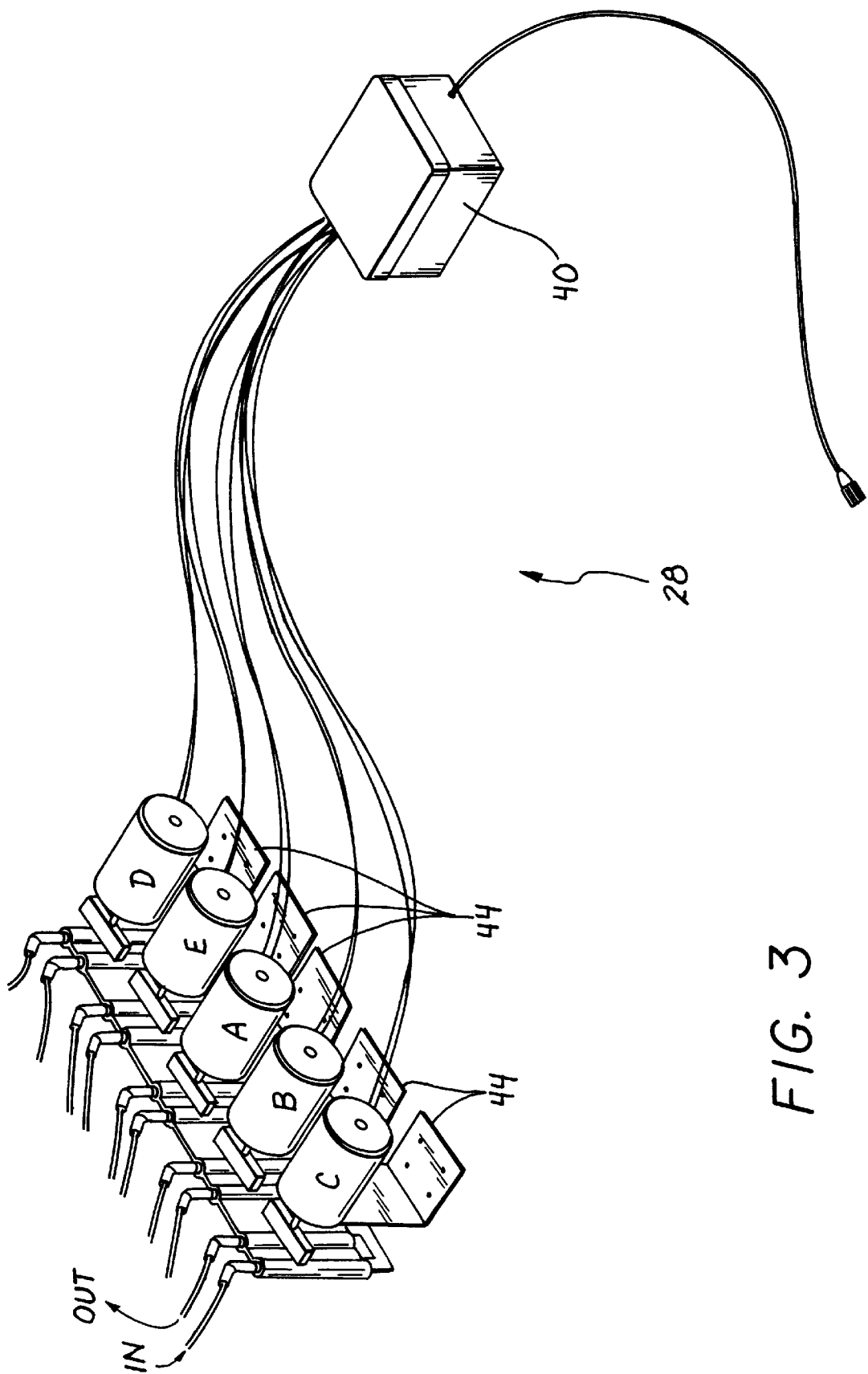
FIG. 3 is a perspective view illustrating a first inventive arrangement of the solenoid pinch valves of the present invention.
Figure 4:
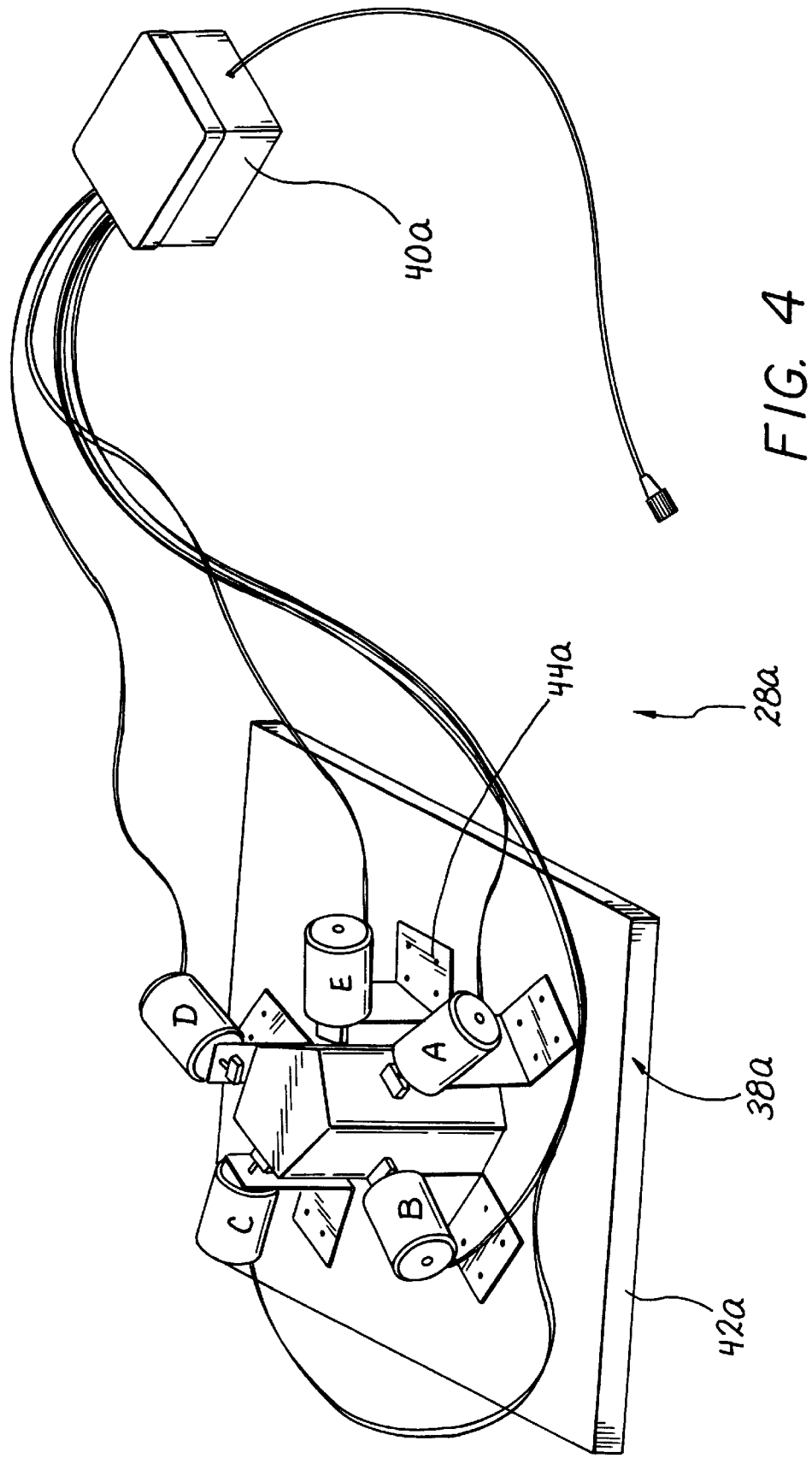
FIG. 4 is a perspective view illustrating a second inventive arrangement of the solenoid pinch valves of the present invention.

In one embodiment, as illustrated in FIG. 1, the vacuum pressure control system 28 comprises a high vacuum supply 32, a low vacuum supply 34, a solenoid valving system 38, and a solenoid valve controller 40. A positive pressure supply could also be provided, if desired. The solenoid valving system 38 includes five solenoid valves A, B, C, D, and E, in this particular embodiment, which are attached to a support platform 42 by means of brackets 44. However, a fewer or greater number of valves controlling pressures and or vacuum of different levels may be utilized within the scope of the invention, and of course they may be mounted or arranged in any reasonable manner, which would be known to one of ordinary skill in the art. For example, in an alternative embodiment illustrated in FIG. 4, wherein like elements to those of FIG. 3 are identified by like reference numerals, succeeded by the letter a, the solenoid valves are arranged in a generally circular pattern, though operationally they function in an equivalent manner to the arrangement illustrated in FIG. 3. Of course, as would be recognized by those of ordinary skill in the art, many other known equivalent types of valving systems could be utilized as well, particularly if they are capable of automatic actuation by a programmable controller.

Figure 5:
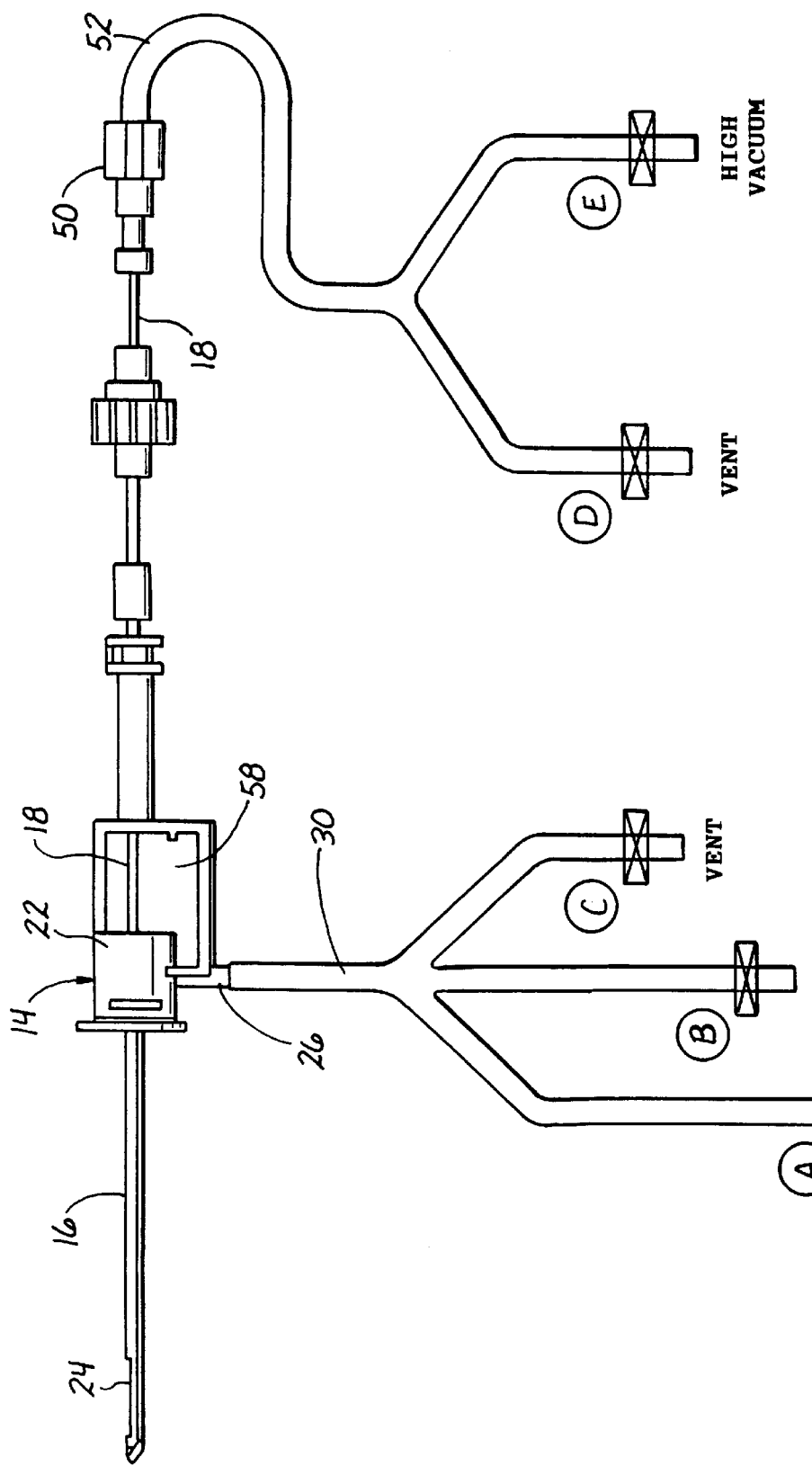
FIG. 5 is a schematic view illustrating a preferred arrangement for attaching the vacuum supply lines to an automated biopsy probe.

With particular reference now to FIGS. 1, 3, and 5, the biopsy instrument 10 includes a proximal aspiration fitting or port 50 (FIGS. 1 and 5) which is adapted for attachment to the vacuum pressure control system 28 (FIG. 1) through a tube or tubing 52. This arrangement permits aspiration of the notch 24 through the lumen 20 (FIG. 16) of the inner cutter 18.

In operation, the distal point 54 of the outer cannula 16 is first moved into position to pierce the lesion or selected tissue (not shown) which is to be sampled The initial global position of the point 54 with respect to the tissue area being sampled is determined by the overall position of the biopsy instrument 10 with respect to the patient. This is accomplished in a manner well known in the art, preferably using a known stereotactic guidance system, and one such preferred method for positioning the point 54 adjacent to the specific lesion region to be sampled is described in U.S. Pat. No. 5,240,011 to Assa, herein incorporated by reference.

Once the point 54 is adjacent to the specific lesion region to be sampled, fine tuning of the location of the notch 24 within the tissue sample is accomplished by advancing or withdrawing the outer cannula 16 along its axis, until the operator is satisfied that the notch 24 is properly positioned for the desired procedure.

During the period of time in which the cannula 16 is being positioned adjacent to the lesion, the inner cutter 18 is maintained in its fully advanced position to close off the notch 24, thus preventing snagging and tearing of the tissue during slow linear movement of the cannula 16. Once the cannula is positioned at the precise location within the lesion at which it is desired to obtain a tissue sample, the tissue specimen cutting procedure is commenced. This procedure is illustrated sequentially in FIGS. 6a through 6f, and in the tables of FIGS. 7 and 8. Initially, as illustrated in FIG. 6a, the cutting cannula 18 is fully retracted proximally to the "start" position, or cutter position "one" of FIG. 7, wherein the distal end of the cutter 18 is disposed at the proximal edge of the tissue cassette housing 22. At the start of the procedure, the cutter 18 is fully retracted to position "one", where solenoid valves A, B, and E are actuated by the controller 40 to be in the closed state, and valves C and D are actuated to be in the open position, as indicated in FIG. 7. In this state, only ambient pressure is being supplied to both the distal probe port 26 and the proximal probe port 50 (FIG. 5). The linear position of the cutting cannula may be detected using any known sensing means such as Hall effect sensors, linear potentiometers, or the like. Alternatively, the necessity for sensors may be eliminated by pre-programming the controller 40 to move the cutting cannula 18 a predetermined distance during each sequential step, simultaneously actuating the valves A–E to the desired state for the particular step.

The cutter 18 is next advanced to position "two" of FIG. 7, as shown in FIG. 6b, preferably by either manual or automatic operation of a drive motor which operates to advance or retract the cutter linearly. Such a drive system is fully described in the aforementioned U.S. Pat. No. 5,526,822, to Burbank et al, for example. As the cutter 18 reaches position "two", the valve controller 40 operates to actuate valves A and E to an open position and valves C and D to a closed position. Valve B remains closed. Thus, referring back to FIGS. 2 and 5, a high vacuum pressure (preferably greater than 18 inches Hg) is supplied to both the distal port 26 and the proximal port 50 as the distal end of the cutter 18 reaches a position just proximal to the tissue receiving notch 24 (see FIG. 6b, which illustrates the cutter 18 in position "two"). This creates a region of very low pressure in the vicinity of the tissue receiving notch 24 and the vacuum lumen 31 (FIG. 16), facilitating the prolapse of tissue immediately adjacent to the notch 24 into the interior of the outer cannula 16. Once the tissue is fully prolapsed into the notch 24, the prolapsed tissue sample is severed from the main tissue mass by the advancement of the cannular inner cutter 18 (FIG. 6c), actuated automatically at the appropriate time by the control unit 40, past the notch 24. The cutter drive motor (not shown) may, at this juncture, operate to rotate the cutter 18 as desired to assist in severing the tissue sample. Such a cutter drive motor, which may be actuated either manually or automatically, is shown and described in the aforementioned U.S. Pat. No. 5,526,822, to Burbank et al. After being severed from the tissue mass, the tissue sample is packed into the distal end of the lumen 20 of the inner cutter 18 as the inner cutter moves forward past the distal edge of the notch 24, to position "three" of FIG. 7, illustrated in FIG. 6c. As the cutter 18 approaches position "three", the controller 40 actuates the valves as necessary such that valves A, B, and D are closed and valves C and E are open. Thus, referring again to FIGS. 2 and 5, ambient pressure is supplied through valve C to the distal port 26, while high vacuum pressure from supply 32 is provided through valve E to the proximal probe port 50. The high vacuum pressure supplied through the cutter lumen 20 from the proximal port 50 functions to retain the tissue specimen in the lumen 20 during the ensuing transport of the cutter and specimen proximally to a suitable tissue receptacle (not shown) in a tissue chamber 58.

FIG. 6d illustrates the inner cutter 18 in position "four", which is the same as position "three", but as the cutter is beginning to retract proximally for delivery of the tissue sample. The tissue sample is retained in the inner cutter 18 as it is withdrawn proximally toward the tissue cassette housing 22, by friction with the inner walls of the cannula, and by suction pressure within the lumen 20 caused by the open valve E. This suction retention force greatly improves efficiency of transportation of the specimen.

As the inner cutter 18 is withdrawn through the housing 22, it passes through cutter position "five", illustrated in FIG. 6e. In cutter position "five", as indicated in FIG. 7, valves B and D are actuated to the open state, while valves A, C, and E are closed. Thus, referring once again to FIGS. 2 and 5, it is seen that a low vacuum pressure (preferably 1–5 inches Hg.) is supplied to the distal probe port 26, while the proximal probe port 50 is open to ambient pressure. Hence, a low vacuum pressure region is created in the vacuum lumen 31, and is communicated to the distal end of the cannula 16 proximate to the tissue receiving notch 24 through apertures 56. This applied "constant" low suction pressure to the region adjacent the notch 24 is advantageous in that it assists in drawing blood, tissue bits, and other by-products of the cutting operation from the procedure site proximally through the vacuum lumen 31 such that it exits through the distal port 26 into a medical waste receptacle (not shown) or the like, thereby preventing the blood and other waste from either clogging lumens 20 and 31 or apertures 56, or traversing proximally through the cutter lumen and discharging with the tissue specimen into a specimen receptacle (not shown), such as a tissue cassette, for example, within the tissue chamber 58 in the housing 22. Bleeding can cause at least three problems; namely, clogging of lumens or apertures within the probe, interference with a practitioners ability to collect a tissue specimen, and blood not drained into a collection reservoir may damage delicate mechanical/electrical equipment below. A tubular knock-out pin (not shown) may be used to assist in discharging the tissue specimen into the tissue receptacle.

Once the intact tissue specimen has been obtained, the cutting cannula 18 is returned proximally to its start position "six", which is the same as position "one", as illustrated in FIG. 6f, and the valves are maintained in the same state as in position "five". Thus, low vacuum pressure continues to be supplied to the outer cannula adjacent to the notch 24 from the vacuum lumen 31, such that medical waste continues to be drawn from the procedural site through the lumen 31 and distal port 26 into an appropriate waste receptacle, away from the biopsy instrument and delicate equipment.

At this juncture, referring in particular to FIG. 8, a decision is made by medical practitioner conducting the procedure as to whether more tissue specimens are desired. If the decision is negative, then the procedure is concluded and the probe 14 is withdrawn from the patient. If the decision is positive then the cutter is returned to position "two", the controller 40 actuates the valves to their position "two" states as indicated in FIG. 7, and the sequence is repeated for obtaining a second specimen. The sequence may be repeated as many times as required until the desired number of tissue specimens have been obtained. Typically, the outer cannula 16 may be rotated through a predetermined angle between each cutting sequence, in order to obtain tissue specimens from sites disposed at each of various angular orientations of the tissue receiving notch 24 relative to the long axis of cannula 16. Alternatively, the outer cannula may be moved between each sequence, if desired, without complete removal from the patient, in order to obtain additional tissue specimens from tissue sites at different locations. These possibilities are discussed more fully in U.S. Pat. No. 5,526,822 and in the other patent applications referenced supra.

Figure 9A:
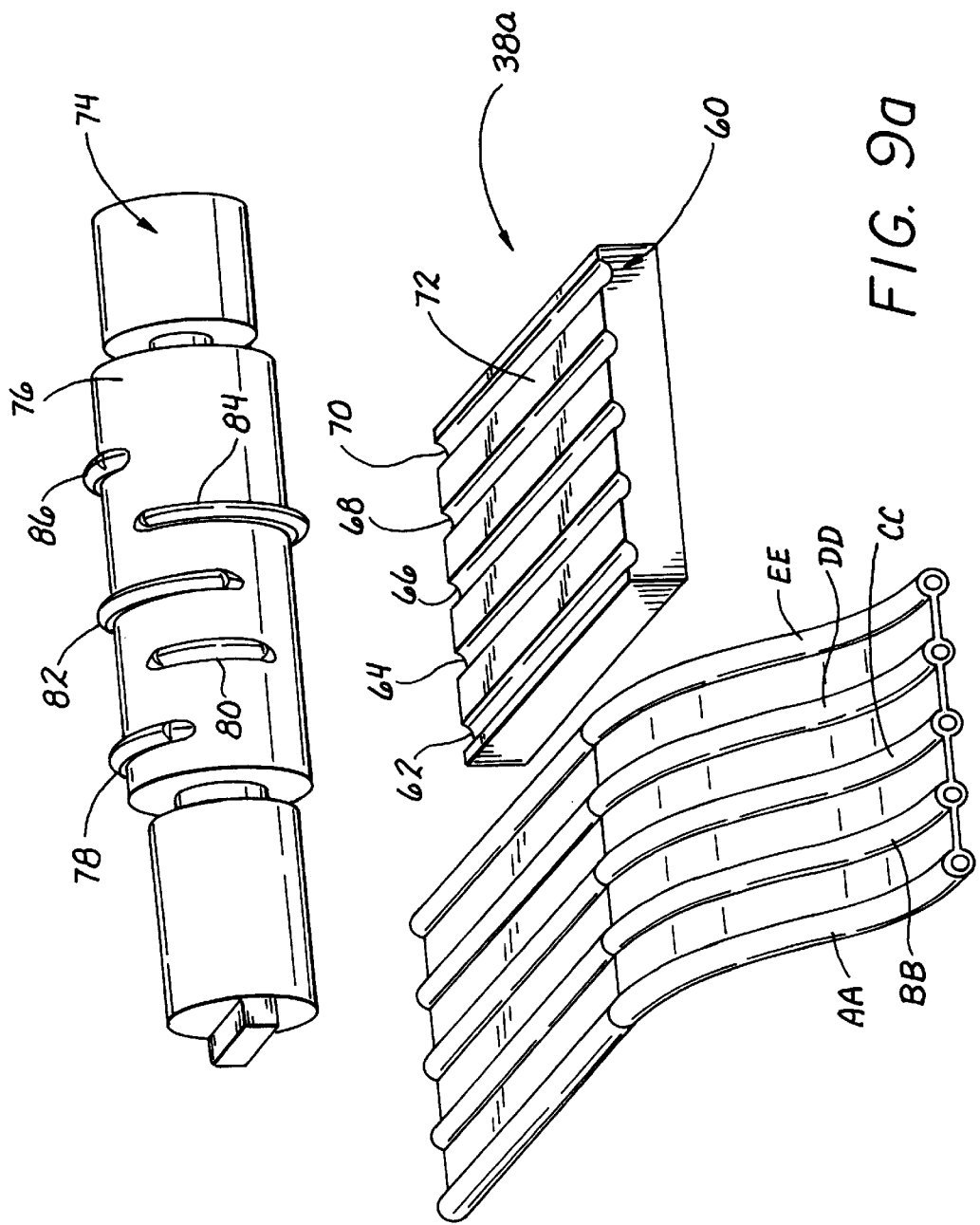
FIGS. 9A and 9B are perspective views illustrating an alternative mechanical camming embodiment for controlling the flow through each vacuum supply line in the system of the invention.
Figure 9B:
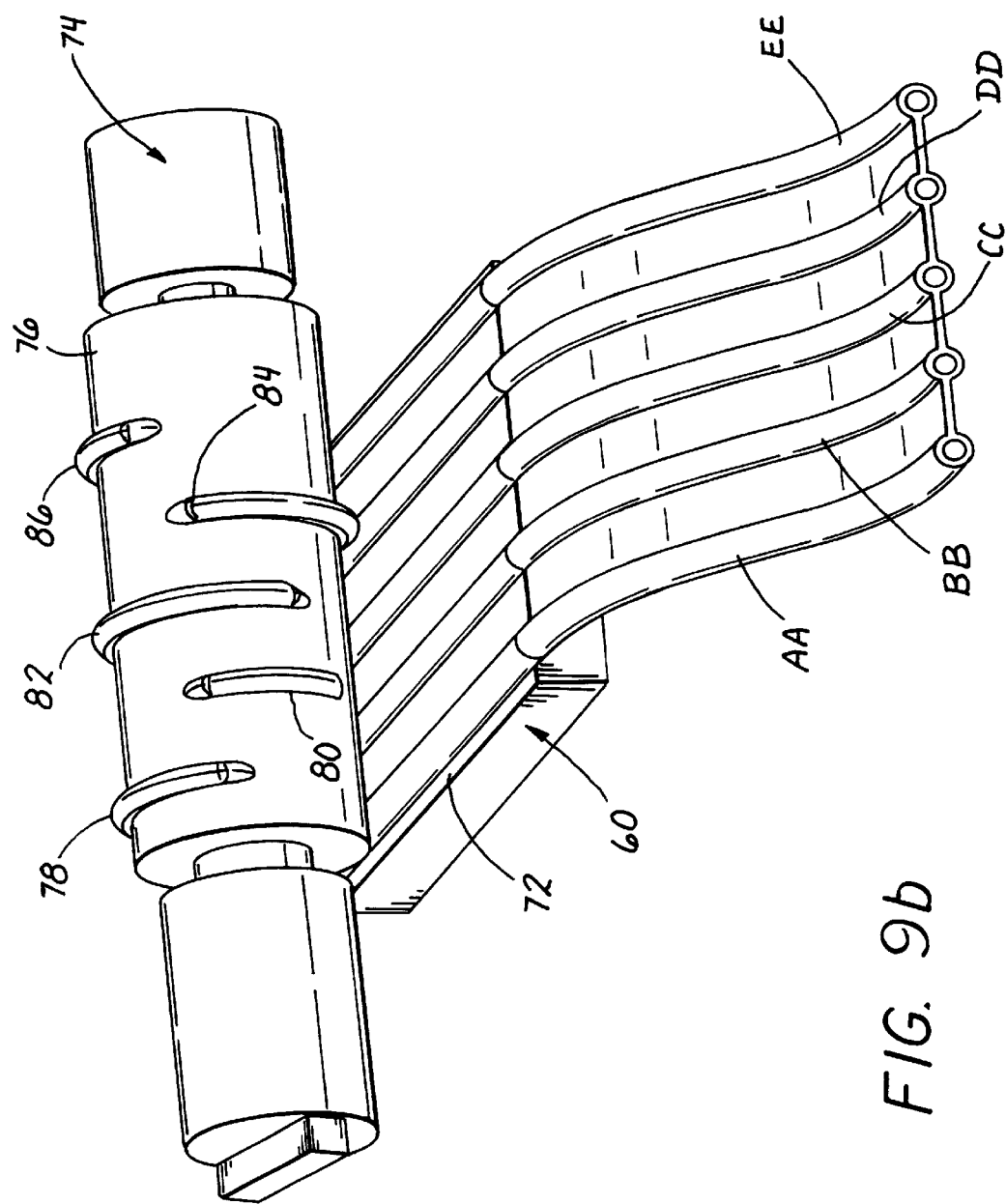
Figure 10:
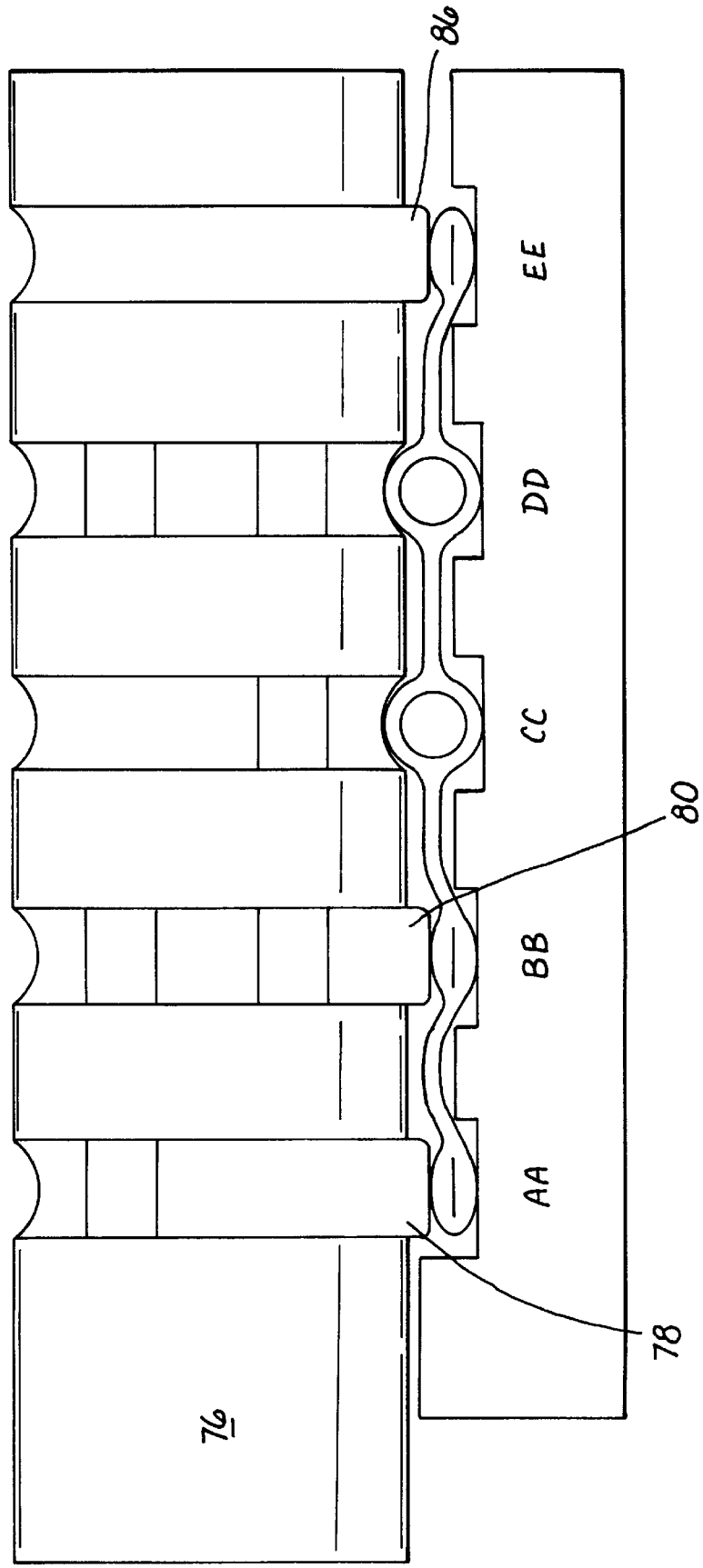
FIG. 10 is a schematic end view illustrating operation of the camming embodiment shown in FIG. 9.
Figure 11:
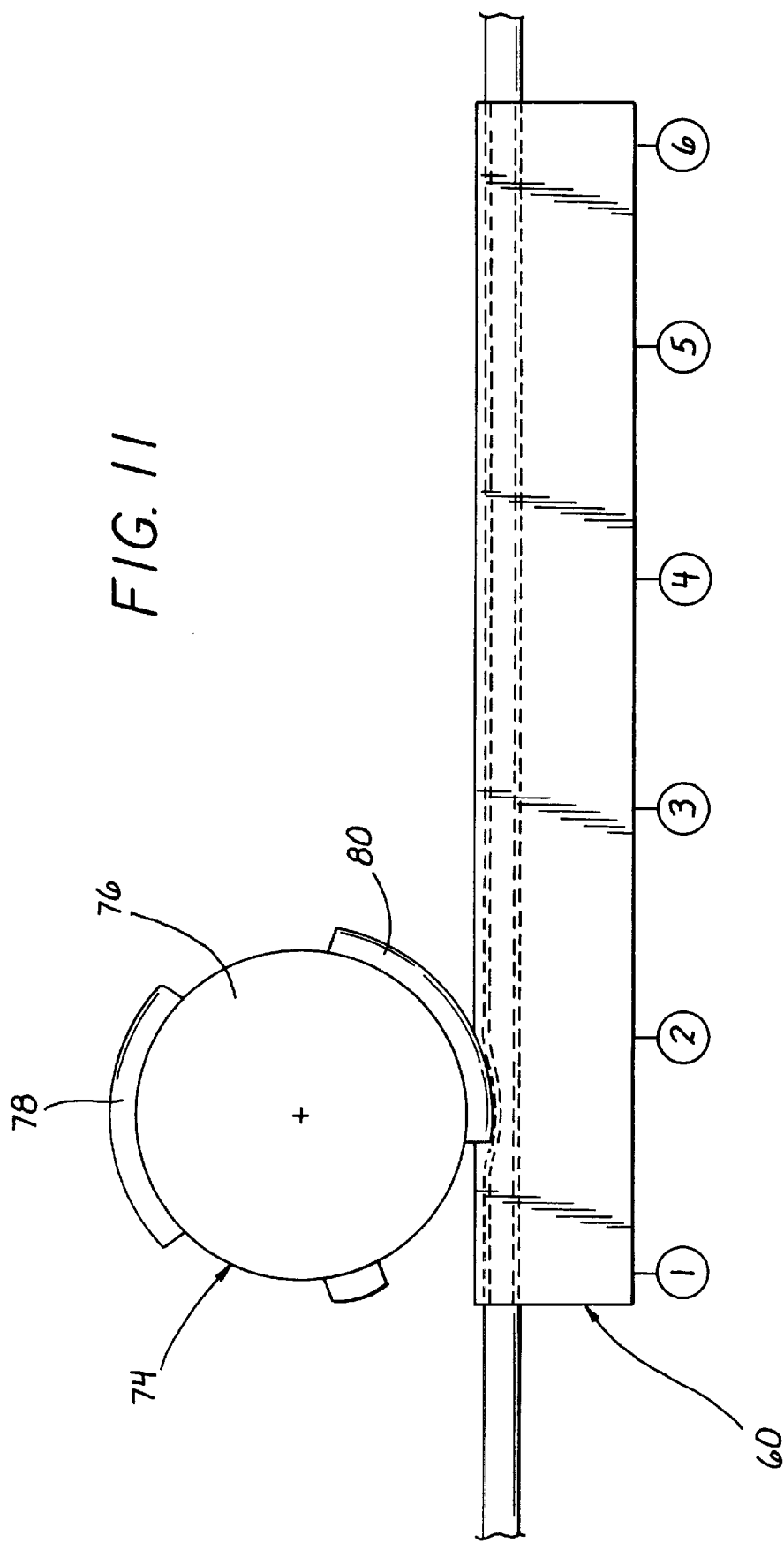
FIG. 11 is a schematic elevational view illustrating operation of the camming embodiment shown in FIG. 9.

FIGS. 9A, 9B, and 10–12 illustrate an alternative mechanical valving arrangement or system 38a, which could be used, for example, in the system illustrated in FIGS. 1–8. The valving system 38a comprises a valve platform 60 having a plurality of flow channels 62, 64, 66, 68, and 70 formed longitudinally in an upper surface 72 thereof. A plurality of flow passages, preferably comprising elastomeric tubes AA, BB, CC, DD, and EE, are adapted to be disposed in corresponding channels 62, 64, 66, 68, and 70, respectively (FIGS. 9B and 10). A rotatable spool 74, having a camming surface 76 and a plurality of circumferentially and axially spaced cams 78, 80, 82, 84, and 86 is adapted to roll linearly along the lengths of the tubes AA, BB, CC, DD, and EE. When assembled, the system 38a is configured so that, as the spool 74 is rotated linearly along the tubes AA, BB, CC, DD. EE, the tubes remain fully expanded and open to fluid flow except when contacted by a corresponding protruding cam, at which point the cam compresses or pinches the tube with which it comes into contact, preventing fluid flow through the tube. Thus, as illustrated in FIG. 10, cams 78, 80, and 86 are in contact with tubes AA, BB, and EE, respectively, thereby closing or shutting off flow through those tubes. The remaining tubes CC and DD, being in abutting relationship only with the camming surface 76 (or, alternatively, a groove formed in the camming surface 76, are fully expanded, and thus in an open state.

Figure 2:
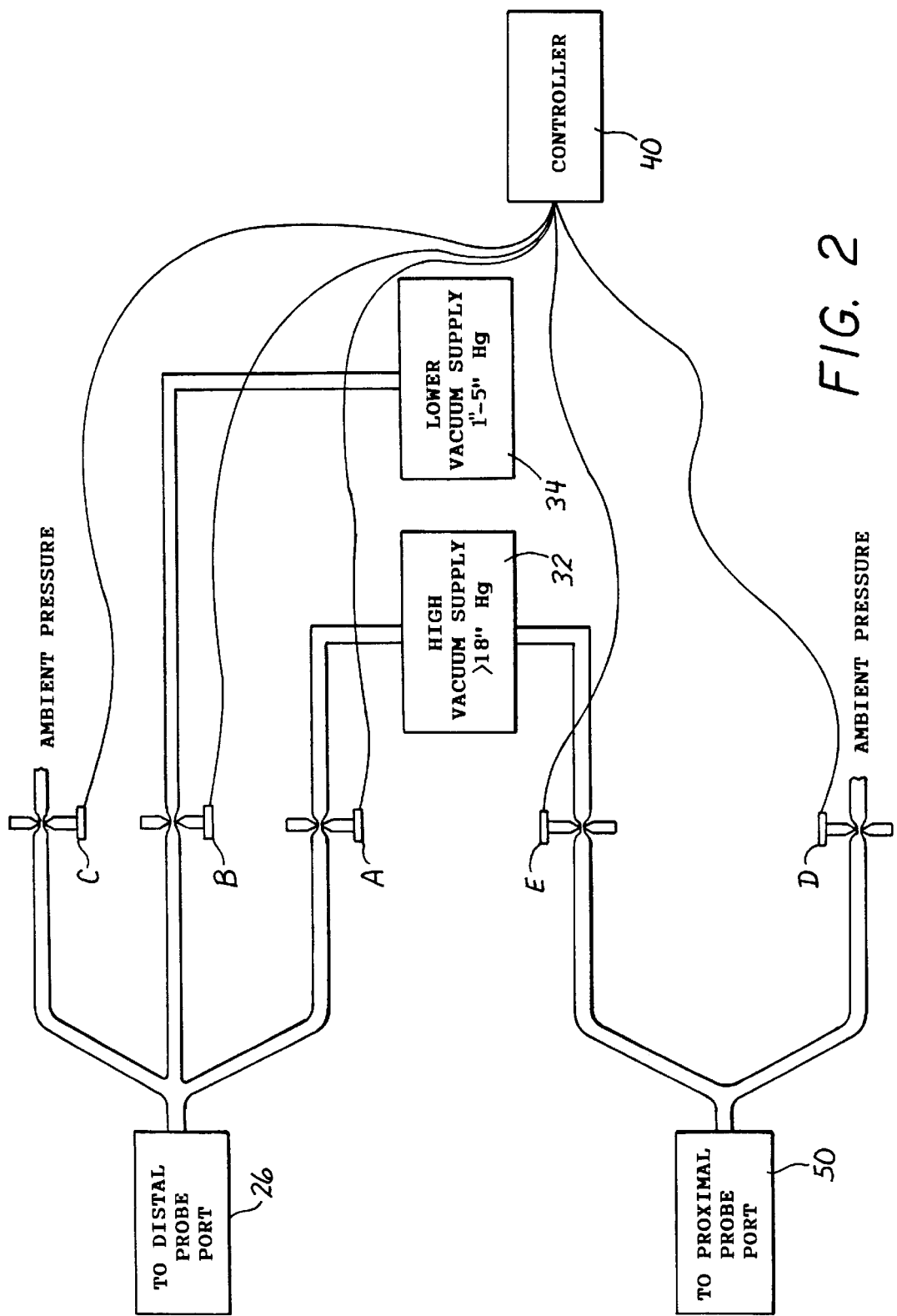
FIG. 2 is a schematic view illustrating the vacuum supply lines and solenoid pinch valves which comprise one embodiment of the present invention.

In operation, the system 38a described supra and illustrated in FIGS. 9A, 9B, and 10–12 may be utilized in place of system 38 illustrated in FIG. 2, wherein the tubes AA, BB, CC, DD, and EE function equivalently to the corresponding solenoid valves A, B, C, D, and E, respectively. The cams 78, 80, 82, 84, and 86 corresponding to each of the tubes AA, BB, CC, DD, and EE are each arranged to be of a particular length and to be disposed to occupy a particular circumferential portion of the camming surface 76 such that the controller 40 may be programmed to rotate the spool 74 through a particular angular distance for each of the positions "one" through "six" indicated in the table of FIG. 7, so that each of the tubes AA through EE, by virtue of the particular arrangement of cams 78, 80, 82, 84, and 86, is opened or closed as indicated by the table in FIG. 7 for the particular position of the cutting cannula 18. For example, when the cutting cannula 18 is at position "one", as illustrated in FIG. 6a and FIG. 10, the controller 40 actuates the spool 74, by means of a stepper motor (not shown) or the like, to rotate through a particular angular distance to the position denoted as "1" on the valve platform 60 (see FIGS.

10 and 11), such that the cam 78 contacts tube AA and pinches it to the closed position, the cam 80 pinches tube BB to the closed position, the cam 86 pinches tube EE to the closed position, and the remaining two tubes CC and DD are not contacted by their corresponding cams 80 and 82, respectively, so that they remain in an open state. As is the case with the FIG. 1 embodiment, therefore, tube CC vents the distal port 26 to ambient pressure, while the tube DD likewise vents the proximal port 50 to ambient pressure. Then, when the cutter moves to position "two", the spool is rotated to a corresponding position "2" (FIG. 11) along the valve platform 60 such that the cams 78, 80, 82, 84, and 86 are displaced to a configuration wherein tubes AA and EE are open and the remaining tubes are closed. This procedure continues through the entire sequence illustrated in FIG. 8, and, of course, may be repeated as many times as necessary to obtain the desired number of tissue specimens.

Figure 12:
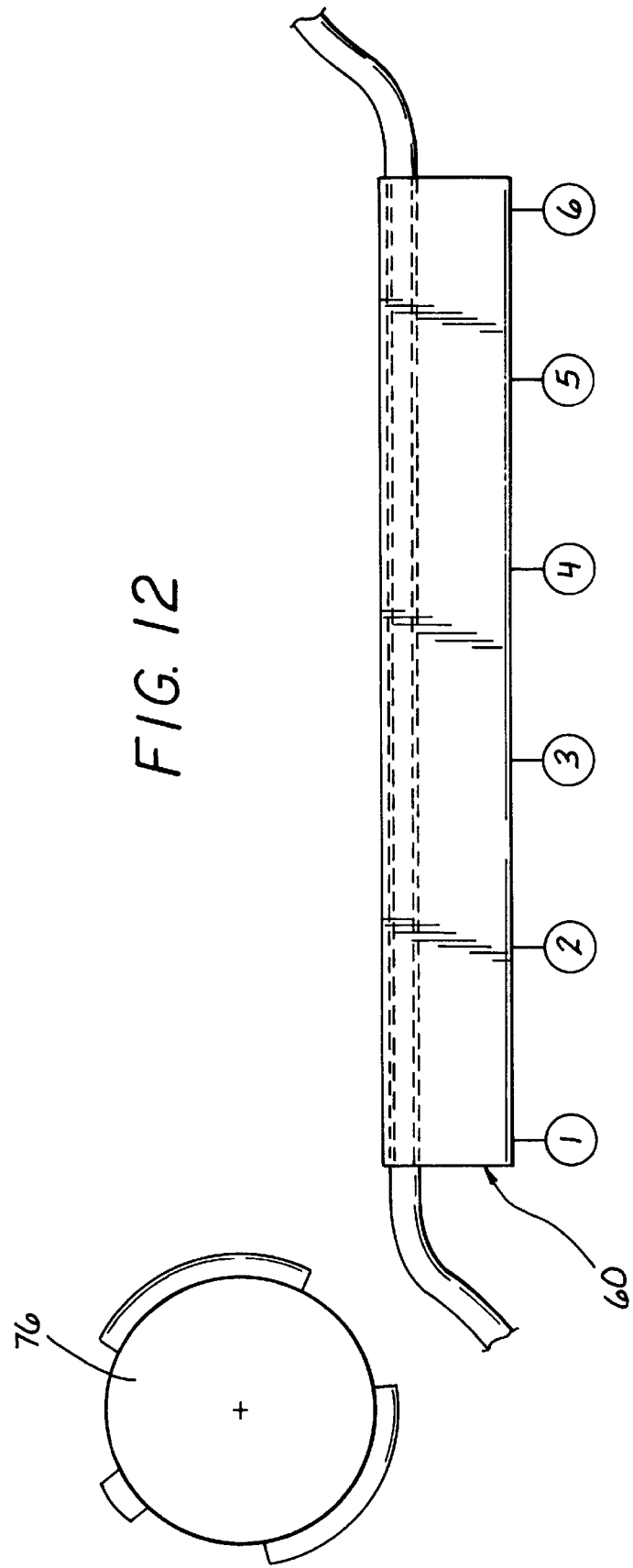
FIG. 12 is a schematic elevational view illustrating the camming embodiment of FIG. 9 in a disengaged state.

As shown in FIG. 12, an advantage of the mechanical valving embodiment is that the cam spool 74 is preferably configured to be readily disengaged from the valve platform 60 in order to enable easy removal and replacement of the tube sets AA, BB, CC, DD, and EE and for maintenance.

Figure 13:
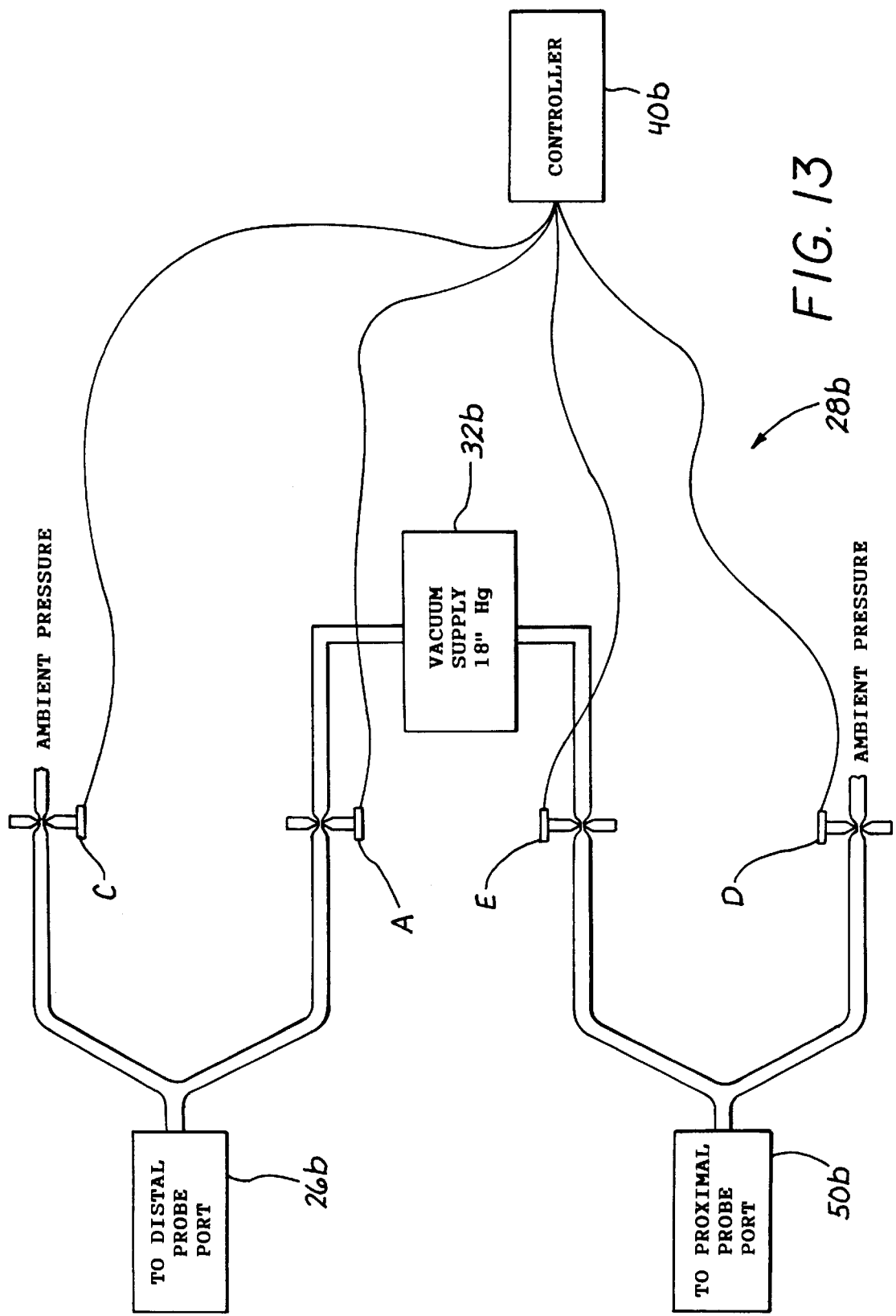
FIG. 13 is a schematic view similar to FIG. 2, illustrating the vacuum supply lines and solenoid pinch valves which comprise a modified, presently preferred embodiment of the invention.
Figure 14:
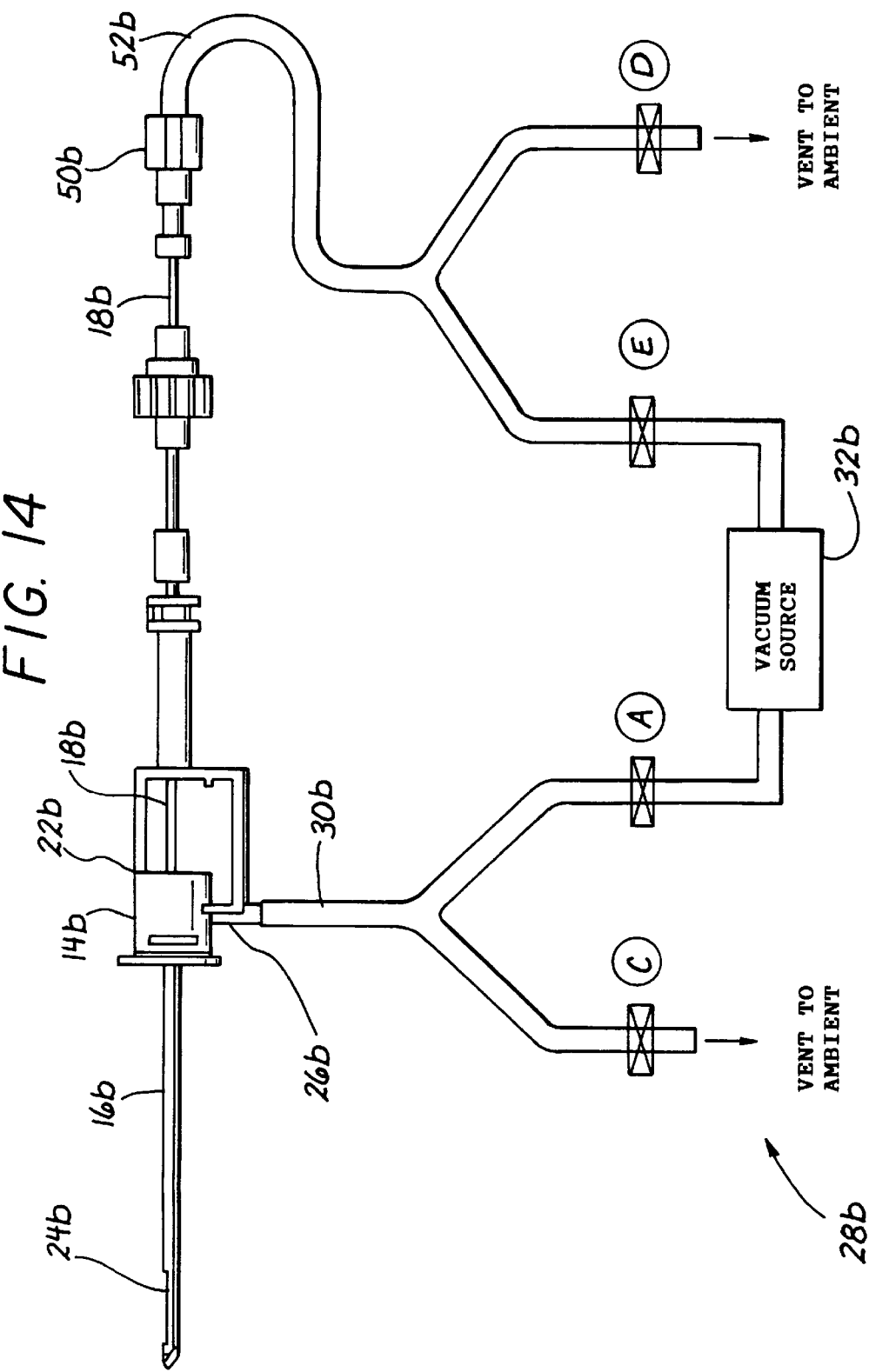
FIG. 14 is a schematic view similar to FIG. 5, illustrating a modified arrangement for attaching the vacuum supply lines to an automated biopsy probe, according to the embodiment of FIG. 13.

Another, presently preferred embodiment of the inventive vacuum pressure control system is illustrated in FIGS. 13–15. In this embodiment, like elements to those of the system of FIGS. 1–5 are designated by like reference numerals, succeeded by the letter b. Like valves are designated by the same letters as in FIGS. 1–5.

The modified vacuum pressure control system 28b of FIGS. 13–15 is similar in many respects to the system 28 of FIGS. 1–5, but eliminates the low vacuum supply 34 and associated valve B. In operation, with reference to FIGS. 6a–6f, 8, and 13–16, once the outer cannula 16, 16b has been properly positioned at the desired tissue sampling site, the inner cannular cutter 18, 18b is fully retracted proximally to the "start" position, or cutter position "one" of FIGS. 6a and 15, wherein the distal end of the cutter 18, 18b is disposed at the proximal edge of the tissue cassette housing 22, 22b. As the cutter 18, 18b approaches position "one", the valves A, C, D, and E are appropriately actuated by the controller 40b such that valves A and E are closed while valves C and D are open, as indicated in FIG. 15. This state is the same as that in the first embodiment, and permits only venting of each of the distal and proximal ports 26b and 50b, respectively, to ambient pressure.

The cutter 18, 18b is next advanced to position "two" of FIG. 15, as illustrated in FIG. 6b. As the cutter 18, 18b approaches position "two", the valve controller 40b operates to actuate valves A and E to an open position and valves C and D to a closed position. Thus, as in the first embodiment of FIGS. 1–5, a high vacuum pressure is supplied to both the distal port 26, 26b and the proximal port 50, 50b as the distal end of the cutter 18, 18b passes a position just proximal to the tissue receiving notch 24, 24b. This creates a region of very low pressure in the vicinity of the tissue receiving notch 24, 24b, communicated through both the vacuum lumen 31 and apertures 56 and the cutter lumen 20 (FIG. 16). This low pressure region facilitates the prolapse of tissue immediately adjacent to the notch 24, 24b into the interior of the outer cannula 16. Once the tissue is fully prolapsed into the notch 24, so as to fill the tissue receiving cavity formed in the interior of the outer cannula 16, the prolapsed tissue sample is severed from the main tissue mass by the advancement of the inner cannular cutter 18, 18b, actuated manually or automatically at the appropriate time by the control unit 40, past the notch 24, 24b, to thereby sever the prolapsed tissue sample from the main tissue mass. The cutter drive motor (not shown) may, at this point, operate to rotate the cutter 18, 18b as desired to assist in severing the tissue sample.

After being severed from the tissue mass, the tissue sample is packed into the distal end of the lumen 20 (FIG. 16) of the inner cutter 18, 18b as the inner cutter moves forward past the distal edge of the tissue notch 24, to position "three" of FIG. 15, illustrated in FIG. 6c. As the cutter 18, 18b approaches position "three", the controller 40b actuates the valves as necessary such that valves A and D are closed, and valves C and E are open. Thus, referring again to FIGS. 13 and 14, ambient pressure is supplied through valve C to the distal port 26, 26b, while high vacuum pressure from supply 32b is provided through valve E to the proximal port 50, 50b. The high vacuum pressure supplied through the cutter lumen 20 (FIG. 16) from the proximal port 50, 50b functions to retain the tissue specimen in the lumen 20 during the ensuing transport of the cutter and specimen proximally to the tissue receptacle chamber 58, 58b.

As the inner cutter 18, 18b is withdrawn through the housing 22, 22b, it passes through cutter position "five", illustrated in FIG. 6e. In this position as indicated in FIG. 15, valves C and E are closed, while valve D is open and valve A is actuated by the controller 40b to cycle on and off, so that high vacuum pressure is alternately "pulsed" to the distal probe port 26b. An advantage of pulsing vacuum pressure through the vacuum lumen 31 into the tissue receiving chamber of outer cannula 16 when the inner cutter 18, 18b is at or proximal to position 5 is that the vacuum lumen 31 is kept patent (i.e. not clogged with blood and other bits of tissue generated by the tissue cutting procedure) and the blood and tissue waste is drawn through the vacuum lumen 31 and into a medical waste receptacle, rather than exiting from the proximal end of the cutter lumen 31, and thereby interfering with the tissue specimen retrieval process or otherwise inconveniencing the practitioner. The inventors have discovered that the on/off cycle time is dependent upon a number of factors, and a cycle of 1 second on and 1 second off is presently preferred for the illustrated embodiment, wherein the pump constituting the vacuum supply 32b is supplied by Thomas Industries and is rated to create a vacuum of 26" Hg at a flow rate of 37½ SCFH. Factors involved in determining cycle time include the requirement that for effective removal of blood and tissue debris approximately 50–90% of the full vacuum pressure available must be generated at the tip of the probe 14 for a short period of time sufficient to aspirate away the aforementioned blood and debris. Thus, the volume of tubing from the vacuum source 32b and the probe tip must be taken into account, as well as the vacuum pump capacity. If a pump having a greater capacity and/or tubing of lesser volume were employed the on cycle time could be decreased and/or the off cycle time could be increased. Conversely, if a pump having a lesser capacity and/or tubing of greater volume were employed, the on cycle time would need to be increased and/or the off cycle time would need to be decreased.

While the constant low vacuum embodiment of FIGS. 1–5 is advantageous over the prior art for a number of reasons, the pulsing embodiment of FIGS. 13–15 may even be more advantageous for the purpose of effectively drawing blood and tissue waste away from the procedural site without interfering with tissue specimen recovery. For example, the embodiment shown in FIGS. 13–15 has the advantage of eliminating one valve (valve B) and the need for a source of low vacuum pressure (element 34 in FIGS. 1–5). thereby reducing the cost of production and simplifying operation and maintenance.

Once the intact tissue specimen has been obtained, the cutting cannula 18 is returned proximally to its start position "six", which is the same as position "one", as illustrated in FIG. 6f, and the valves are maintained in the same state as in position "five". Thus, high vacuum pressure continues to be pulsed through the vacuum lumen 31 and to the region adjacent to the notch 24, 24b, such that medical waste continues to be drawn from the procedural site through the lumen 31 and distal port 26, 26b into an appropriate waste receptacle.

As in the case of the first embodiment of FIGS. 1–5, the foregoing procedure may be repeated as many times as necessary to ensure that the desired number of tissue samples have been obtained, as indicated in the logic diagram of FIG. 8.

While this invention has been described with respect to various specific examples and embodiments, it is to be understood that the invention is not limited thereto and that it can be variously practiced within the scope of the following claims.

What is claimed is:

1. An automatic biopsy device, comprising:
    a first elongate cannula having a distal end for entering tissue and a notch located proximally of said distal end for receiving a portion of the tissue which is positioned adjacent to said notch;
    a second elongate cannula disposed coaxially with said first cannula, said second cannula being slidable axially along the first cannula for cutting the portion of tissue protruding into said notch when said second cannula slides past said notch, thereby depositing the portion of cut tissue within said first elongate cannula proximal to said first cannula distal end;
    a source of vacuum pressure for selectively delivering vacuum pressure to a region within said first elongate cannula adjacent to said notch;
    at least one passage for fluidly connecting the source of vacuum pressure to the region adjacent to the notch; and
    a controller for controlling the flow of vacuum pressure to said region during a biopsy procedure such that the ability to successfully obtain and transport a tissue sample proximally from said notch to a tissue sample receptacle is enhanced, said controller operating during said procedure without user input to automatically adjust the flow of vacuum pressure to said region according to a predetermined schedule based upon an axial position of said second cannula relative to said first cannula.

2. The automatic biopsy device as recited in claim 1, wherein said first elongate cannula comprises an outer hollow cannula and said second elongate cannula comprises an inner cutter.

3. The automatic biopsy device as recited in claim 1, wherein said at least one passage comprises a vacuum lumen having a distal end and a proximal end, the distal end of the vacuum lumen communicating with the region within said first cannula adjacent to the notch through at least one aperture disposed between said region and said vacuum lumen.

4. The automatic biopsy device as recited in claim 3, wherein said at least one passage further comprises a lumen extending through said second elongate cannula, the biopsy device further comprising a distal aspiration port which communicates with said vacuum lumen, and a proximal aspiration port which communicates with said second elongate cannula lumen, the source of vacuum pressure fluidly communicating with each of said distal and proximal aspiration ports.

5. The automatic biopsy device as recited in claim 4, and further comprising a first valve for selectively permitting or shutting off the flow of vacuum pressure through said vacuum lumen, and a second valve for selectively permitting or shutting off the flow of vacuum pressure through said second elongate cannula lumen, said controller actuating each of said first and second valves in order to selectively manage the flow of vacuum pressure to the region adjacent to said notch during a biopsy procedure.

6. The automatic biopsy device as recited in claim 5, wherein said first and second valves are independently actuated by said controller responsive to the position of said second cannula during a biopsy procedure.

7. The automatic biopsy device as recited in claim 5, and further comprising:
    a third passage for venting said distal probe port to ambient, said third passage having a third valve therein for selectively opening and closing said third passage; and
    a fourth passage for venting said proximal probe port to ambient, said fourth passage having a fourth valve therein for selectively opening and closing said fourth passage;
    wherein said third and fourth valves are independently actuated by said controller responsive to the position of said second cannula during a biopsy procedure.

8. The automatic biopsy device as recited in claim 5, (and) wherein said source of vacuum pressure comprises a first source of vacuum pressure, said automatic biopsy device further comprising a second source of vacuum pressure, the vacuum pressure from said second source being of a lower negative pressure than the vacuum pressure from the first source, vacuum pressure from the second source of vacuum pressure being selectively deliverable to said distal aspiration port through a valve independently controlled by said controller.

9. The automatic biopsy device as recited in claim 1, wherein said source of vacuum pressure generates a vacuum pressure of greater than about 18 inches Hg.

10. An automatic biopsy device, comprising:
    a cannula having a distal end for entering tissue and a notch disposed in said distal end for receiving a portion of the tissue which is positioned adjacent to said notch;
    a cutter positionable and operable for cutting the portion of tissue protruding into said notch, thereby depositing the portion of cut tissue within the distal end of said first cannula;
    a proximally disposed tissue receiving chamber;
    a source of vacuum pressure for selectively delivering vacuum pressure to a region within said first elongate cannula adjacent to said notch;
    a passage for fluidly connecting the source of vacuum pressure to the region adjacent to the notch;
    a valve for controlling the flow of vacuum pressure through said passage; and
    a controller for automatically controlling said valve between an open state and a closed state to thereby selectively control the flow of vacuum pressure to said region during a biopsy procedure, said controller operating during said procedure without user input to automatically actuate said valve in order to adjust the flow of vacuum pressure to said region according to a predetermined schedule based upon a position of said cutter relative to said cannula.

11. The automatic biopsy device as recited in claim 10, wherein said cannula comprises an outer hollow cannula and said cutter comprises an inner elongate cannula slidably disposed within said outer cannula.

12. The automatic biopsy device as recited in claim 10, and further comprising a vacuum lumen having a distal end and a proximal end, the distal end of the vacuum lumen communicating with the region within said cannula adjacent to the notch through at least one aperture.

13. The automatic biopsy device as recited in claim 12, wherein:

said cannula comprises an outer hollow cannula and said cutter comprises an inner elongate cannula slidably disposed within said outer cannula;

said passage comprises two passages, a first passage including said vacuum lumen and a second passage including a lumen extending through said inner elongate cannula, the biopsy device further comprising a distal aspiration port which communicates with said vacuum lumen, and a proximal aspiration port which communicates with said inner elongate cannula lumen, the source of vacuum pressure fluidly communicating with each of said distal and proximal aspiration ports.

14. The automatic biopsy device as recited in claim 13, and further comprising a first valve for selectively permitting or shutting off the flow of vacuum pressure through said vacuum lumen, and a second valve for selectively permitting or shutting off the flow of vacuum pressure through said inner elongate cannula lumen, said controller actuating each of said first and second valves between an open position and a closed position in order to selectively manage the flow of vacuum pressure to the region adjacent to said notch during a biopsy procedure.

15. The automatic biopsy device as recited in claim 14, wherein said first and second valves are independently actuated by said controller responsive to the position of said inner cannula during a biopsy procedure.

16. The automatic biopsy device as recited in claim 14, wherein the first and second valves are both actuated by the controller to the closed position at the start of a biopsy procedure.

17. The automatic biopsy device as recited in claim 14, wherein when a distal end of the inner elongate cannula is disposed just proximal to said notch, in preparation for severing a tissue sample, the first and second valves are both actuated to the open position in order to deliver maximum vacuum pressure to the vicinity of said notch, to thereby draw tissue into the notch.

18. The automatic biopsy device as recited in claim 14, wherein when a distal end of the inner elongate cannula is disposed distally of said notch, after severance of a tissue sample, the first valve is actuated to the closed position and the second valve is actuated to the open position, to enhance transport of the tissue sample proximally as the inner cannula is withdrawn proximally.

19. The automatic biopsy device as recited in claim 14, wherein when a distal end of the inner elongate cannula is disposed in the tissue receiving chamber, the first valve is actuated to cycle between the open and closed positions and the second valve is actuated to the closed position.

20. The automatic biopsy device as recited in claim 14, and further comprising a low pressure vacuum source, a flow line between said low pressure vacuum source and said distal aspiration port, and a third valve for controlling flow in said flow line, said third valve having an open state and a closed state, and being selectively actuated by said controller, wherein when the distal end of the inner cutting cannula is disposed in the tissue receiving chamber, the first and second valves are both actuated to the closed position and the third valve is actuated to the open position.

21. A method of controlling vacuum pressure to an automatic biopsy device, said device comprising a first cannula having a distal end for entering tissue and a tissue-receiving notch, a second cutting cannula having a distal end and being disposed coaxially with the first cannula, the second cutting cannula having a lumen, a source of vacuum pressure, a vacuum lumen communicating with a region in said first cannula adjacent to said notch, a distal aspiration port communicating with said vacuum lumen, and a proximal aspiration port communicating with said second cannula lumen, the method comprising:

a) opening both said vacuum lumen and said cutting cannula lumen to the flow of vacuum pressure when the distal end of the cutting cannula is disposed proximal to said notch, before severing of a tissue sample has commenced;

b) closing the vacuum lumen to the flow of vacuum pressure while keeping the cutting cannula lumen open to the flow of vacuum pressure once the distal end of the cutting cannula has traversed distally of the notch and the tissue sample has been severed; and c) closing the cutting cannula lumen to the flow of vacuum pressure once the distal end of the cutting cannula, carrying the tissue specimen, has been withdrawn proximally to a location to which the tissue specimen is to be delivered.

22. The method as recited in claim 21, wherein steps a) through c) are repeated to obtain an additional tissue sample.

23. The method as recited in claim 21, the vacuum lumen is repeatedly alternated between an open and closed state once the distal end of the cutting cannula, carrying the tissue specimen, has been withdrawn proximally to a location to which the tissue specimen is to be delivered.

* * * * *